United States Patent [19]

Linkow et al.

[11] 4,044,467
[45] Aug. 30, 1977

[54] SYMPHYSEAL-RAMI EDOSTEAL IMPLANT

[76] Inventors: Leonard I. Linkow, 30 Central Park South; Joni Chambliss, 58 W. 58 St., both of New York, N.Y. 10019

[21] Appl. No.: 688,012

[22] Filed: June 28, 1976

[51] Int. Cl.² .............................................. A61C 13/00
[52] U.S. Cl. ..................................................... 32/10 A
[58] Field of Search ........................................ 32/10 A

[56] References Cited

U.S. PATENT DOCUMENTS

| 3,748,739 | 7/1973 | Thibert | 32/10 A |
| 3,908,269 | 9/1975 | Christenot | 32/10 A |

Primary Examiner—Robert Peshock
Attorney, Agent, or Firm—James & Franklin

[57] ABSTRACT

A symphyseal-rami endosteal implant comprises a symphysis blade, at least one ramus blade, and at least one intermediate member. The symphysis blade has a first portion adapted to be received in the symphysis bone and a second portion defining at least one projecting post. The ramus blade has a first portion adapted to be received in a ramus bone and a second portion defining a rod adapted to extend generally parallel to the occlusal plane when the ramus blade first portion is received in the ramus bone. The intermediate member has generally vertically aligned first and second portions, the first portion being adapted to engage, slide longitudinally with respect to, and be secured to a length of the rod and the second portion being adapted to engage and be secured to an associated symphysis blade post.

30 Claims, 2 Drawing Figures

SYMPHYSEAL-RAMI EDOSTEAL IMPLANT

BACKGROUND OF THE INVENTION

The present invention relates to endosteal implants, and more particularly to symphyseal-rami endosteal implants.

The conventional symphyseal-rami implant (commonly called a ramus frame implant) is a one-piece endosteal implant designed for use in the edentulous mandible. The implant is typically used where conventional endosteal or sub-periosteal implantation cannot be used because of inadequate bone, anatomical anomalies, or medical or economic considerations. The implant comprises a bar of biocompatible metal curved to follow generally the occlusal plane and having ends extending directly into each ramus and, depending from the center thereof, a symphysis portion. The tripodial design offers exceptional stability, the bar being supported by the symphysis anteriorly and the two ascending rami posteriorly. The frame or curved bar continuous with the endosteal portions lying above the gingiva supports the patient's mandibular prosthesis. The conventional implant and the technique for using the same is described in an article by Robert E. Nelson entitled "The Ramus Frame Implant for Stabilizing Impossible Mandibular Dentures" (*Oral Implantology*, Vol. IV, No. 4, Spring 1974, pages 475–503).

While the conventional one-piece implant has proven to be a valuable new technique for aiding "denture cripples" who could not otherwise be provided with dentures, it has not proven to be entirely satisfactory. Obviously it is desirable that the endosteal or bone-penetrating portions of the implant be disposed in the mandible in a totally passive manner, i.e., without exerting lateral or torque forces on the bone. This cannot be accomplished with the conventional one-piece frame which must be bent and sprung into place, thereby causing excessive pressure to the buccal plate of bone in the ramus areas. Indeed, the bending of the frame causes a considerable weakening of the metal as well as surface scratches thereon. Furthermore, to allow seating of the ramus implant, the bone grooves must be overextended, thus requiring a great deal of undue trauma to the bone during insertion. Finally, due to differences in the size and curvature of the symphysis area of bone, the symphysis portion must be adjusted by extensive bending and grinding procedures which necessitate resterilization of the implant before final seating thereof in the bone.

Even after the conventional implant is in place, additional problems present themselves. The soft tissue covering the ascending rami is only loosely attached to the bone, so that the tissue tends to move along the protruding portion of the bar during movement of the mandible. As the surgical metal of the implant is not fully compatible with the soft tissue, there results tissue irritation and tissue inflammation, as well as infiltration of bacteria and germs through the loose seal between the tissue and the metal. Furthermore, if any portion of the implant eventually fails and requires removal, it is necessary to remove the entire implant for repair or replacement.

One recent improvement to such implants involves the separation of the one-piece frame into three pieces: a symphysis blade and two ramus blades. The symphysis blade has a first portion adapted to be received in the symphysis bone, and each ramus blade has a first portion adapted to be received in an associated ramus bone. The symphysis blade has a second portion comprising a solid bar curved to meet the configuration of the symphysis bone and extending toward the ramus blades at each end, while each ramus blade has a second portion comprising a solid bar extending toward the symphysis blade. The ends of the second portions of the blades are adjusted by bending and shortening the opposing ends until they are in contact. The three pieces are then stabilized with overlaying clamps which lock the ends of the second portions together. This modification has not proven to be entirely satisfactory in use as the locking of the second portion ends by the clamp fails to provide sufficient strength to resist the tremendous pressures created by mastication. Furthermore, the three-piece implant, while more easily and more passively inserted than the one-piece implant, still requires considerable adjustments for proper fitting.

To remedy the strength deficiencies of the three-piece implant, it has been proposed to provide a male/female engagement between the ends of the second portions of the blades, each end of the symphysis blade second portion being hollowed to receive an associated projecting end of a ramus blade second portion. However, whereas the early clamping embodiment of the three-piece implant permits the blades to be inserted totally passively, the later male/female version does not, thus re-introducing the torquing problems associated with the conventional one-piece insert.

Accordingly, it is an object of the present invention to provide a symphyseal-rami endosteal implant in which the endosteal portions of the implant can be placed totally passively into bone.

Another object is to provide such an implant which is substantially compatible with the soft tissue covering the ascending rami to minimize tissue irritation and inflammation and provide a closer seal around the protruding implant to protect the bone from infiltration of bacteria and germs.

A further object is to provide such an implant in which a failed portion can be removed and replaced without disturbing the remainder of the implant.

It is also an object to provide such an implant which can be easily inserted in place without requiring any bending of the metal thereof.

It is another object to provide such an implant which is of sufficient structural to withstand the forces generated during mastication.

SUMMARY OF THE INVENTION

It has now been found that the above and related objects of the present invention are attained in a symphyseal-rami endosteal implant comprising a symphysis blade, at least one ramus blade, and at least one intermediate member. The symphysis blade has a first portion adapted to be received in the symphysis bone and a second portion defining at least one projecting post. Each ramus blade has a first portion adapted to be received in a ramus bone and a second portion defining a rod adapted to extend generally parallel to the occlusal plane when the ramus blade first portion is received in a ramus bone. Each intermediate member has generally vertically aligned first and second portions, the first portion being adapted to engage, slide longitudinally with respect to, and be secured to a length of the rod and the second portion being adapted to engage and be secured to an associated symphysis blade post.

In a partial implant embodiment adapted to provide support for only one side of the mouth, the symphysis blade requires only a single projecting post and the implant contains only one ramus blade and one intermediate member; in a full implant embodiment adapted to provide support for both sides of the mouth, the symphysis blade has a spaced pair of projecting posts and the implant has a pair of ramus blades and a pair of intermediate members, each of the intermediate members being associated with a different one of the posts and a different one of the ramus blades.

In a preferred embodiment of the present invention, the rod and the intermediate member first portion engage one another at a point vertically aligned with, but spaced from, the post, and the rod telescopes into the intermediate member first portion. The intermediate member is desirably rotatable about the longitudinal axis of its associated post during insertion of the implant to enable a totally passive insertion of the implant.

Generally adhesive means connect the intermediate member second portion to its associated symphysis blade post and the intermediate member first portion to its associated rod. It is preferred that the intermediate member second portion and its associated post have registering apertures extending generally horizontally therethrough, so that the implant may additionally include at least one transfixation pin passing through the registering apertures to aid the adhesive means in securing the intermediate member to the symphysis blade.

In an embodiment for use with at least one anterior abutment, the implant comprises at least one ramus blade and at least one means for connecting the ramus blade to the anterior abutment. The anterior abutment of symphysis bone extension may comprise either an artifical structure such as the projecting post of a pre-existing symphysis blade or a natural structure such as a tooth. The ramus blade and the connecting means are identical to the ramus blade and intermediate member described above, except that the anterior abutment serves as the symphysis blade post. The second portion of the connecting means is preferably adapted to be rotatable about and to telescopically cooperate with the anterior abutment, and the anterior abutment may be ground as necessary to enable such functioning.

In all of these embodiments the endosteal or blade portions of the implant are not connected to one another at the time they are placed into the bone, thus they can be seated in a totally passive fashion. The introduction of the intermediate or connecting member to connect the anterior and posterior abutments does not disturb the totally passive placement of the endosteal portions as the intermediate or connecting member is preferably capable of rotating about the axis of the symphysis blade post. Furthermore, as each element of the implant may be provided in a variety of different sizes and configurations, all adapted to interlock with one another, adjustments for proper fitting and the need for elongated bone grooves is eliminated. Thus, resterilization of the implant after fitting is not required and a minimal bone groove can be utilized to seat the endosteal portions of the implant, thus causing no undue trauma to the bone and allowing immediate stability and locking-in of the implant prosthesis.

The provision of a tissue-protective outer coating of aluminous porcelain on the neck portion of each blade, intermediate the first and second portions thereof, reduces or eliminates tissue irritation and inflammation and allows a much closer seal to be formed around the protruding implant, thus protecting the bone from infiltration of bacteria and germs.

The telescoping nature of the connections between elements of the implant insures that the implant will possess sufficient structural strength to resist the forces developed during mastication. In any case, if an element of a full implant (for example, the ramus blade or intermediate member) should fail or require removal, that element can easily be removed and replaced without disturbing the other side of the implant. If any blade element of a partial implant should fail, that blade element can easily be removed and replaced without disturbing the other blade element.

DETAILED DESCRIPTION OF THE PREFERRED EMBODIMENTS

Figure 1:
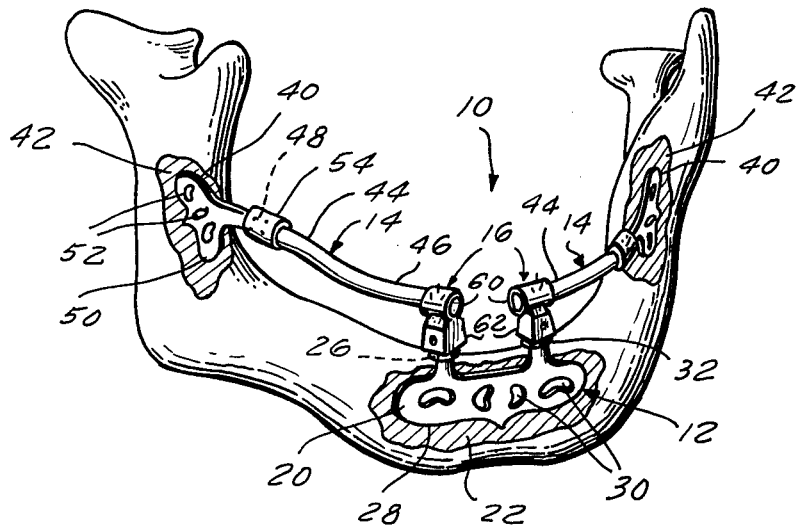
FIG. 1 is a perspective view of a first embodiment of the implant of the present invention seated in a mandible, with portions of the mandible being removed to reveal details of the implant.
Figure 2:
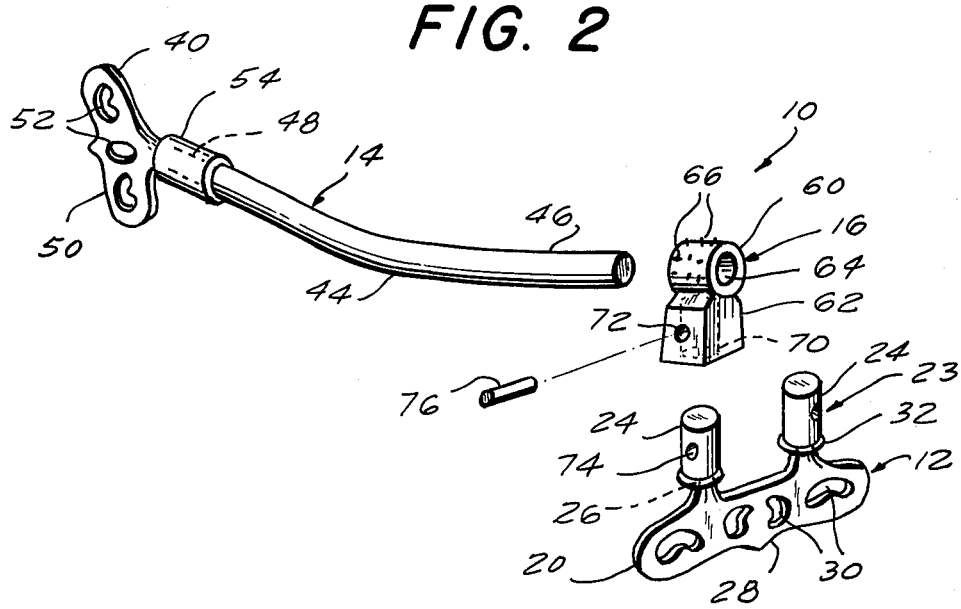
FIG. 2 is an exploded perspective view of the elements of the first embodiment of the implant.

Referring now to the drawings, and in particular to FIGS. 1 and 2 thereof, therein illustrated is a symphyseal-rami endosteal implant or ramus frame generally designated by the numeral 10. Broadly speaking, the implant 10 comprises a symphysis blade generally designated by the numeral 12, a pair of ramus blades generally designated by the numeral 14, and a pair of intermediate members generally designated by the numeral 16, each intermediate member 16 connecting the symphysis blade 12 with a different ramus blade 14. Each of these implant elements will now be described in greater detail.

The symphysis blade 12 comprises a first portion 20 adapted to be received in the symphysis bone 22 (FIG. 1), a second portion generally designated by the numeral 23 and comprised of a spaced pair of upstanding posts 24, and a neck portion 26 connecting each post 24 of the second portion 23 to the first portion 20. The first portion 20 defines a relatively sharp lower edge 28 and a plurality of vents 30 extending therethrough to facilitate bone regeneration and thereby enhance the stabilization of the symphysis blade 12 in the mandible 22. The first portion 20 is configured to utilize the maximum amount of available bone in the symphysis area, and a variety of different symphysis blade designs and shapes may be provided to meet the requirements of different patients in this regard. The first portion 12 is adapted to be received within the symphysis bone 22 with its top portion a millimeter or two below the upper level of the bone 22 to permit bone regeneration thereover and enhance the stabilization of the symphysis blade 12.

The neck portion 26 is preferably covered with a coating or tube of aluminous porcelain 32 (i.e., fused aluminum oxide), a few millimeters in length and adapted to insulate the gum from the metal of the implant. The aluminous porcelain 32 is not only highly compatible with the soft tissue or the gum (not shown) above the mandible 22, but has greater tensile and compression strength than typical dental porcelain. The high strength and high fusion temperature of aluminous porcelain 32 lend themselves readily to the manufacturing procedures for the implant, and indeed the only other materials known to provide comparable tissue tolerance (that is, pure or vitreous carbon) lack the physical properties required.

The symphysis blade second portion 23 comprises a spaced pair of posts 24 adapted to be positioned slightly above the layer of soft tissue (not shown) surrounding the neck portion 26. For reasons which will become apparent hereinafter, the posts 24 are preferably circular in cross section.

Each ramus blade 14 comprises a first portion 40 adapted to be received in a ramus bone 42, a second portion 44 defining a rod 46 adapted to extend generally parallel to the occlusal plane when the ramus blade first portion 40 is received in the ramus bone 42 (FIG. 1), and a neck portion 48 connecting the first and second portions 40, 44. Like the symphysis blade 12 the ramus blade first portion 40 has a relatively sharp edge 50 and a plurality of vents 52 therethrough, and the ramus blade neck portion 48 is preferably covered with a coating or tube of aluminous porcelain 54.

The ramus blade second portion 44 extends generally parallel to the occlusal plane; that is, the imaginary surface that theoretically touches the incisal edges of the incisors and the tips of the occluding surfaces of the posterior teeth. (In fact, the plane or occlusion represents the average curvature of the occlusal surfaces of the teeth in question.) The free end of the rod 46 extends at least as far as the associated post 24 and is adapted to be received within an appropriately configured and dimensioned member, as will be described in further detail hereinafter. The free end of the rod 46 is preferably circular in cross-section and of constant diameter.

A variety of different ramus blades 14 may be provided to enable selection of a ramus blade having a first portion 40 with a size and configuration best adapted to utilize the available bone in the ascending ramus area of a given patient and a second portion 44 which is most parallel to the occlusal plane of a given patient. The ramus blade may be made available in only one length as the exposed end of the rod 46 can easily be cut into an appropriate length for the amount of space existing between the post 24 and the ramus bone 42.

Each intermediate member 16 is adapted to connect the ramus blade rod 46 to an associated symphysis blade post 24 and comprises generally vertically aligned first and second portions 60, 62. The first or upper portion 60 defines a part adapted to engage, slide longitudinally with respect to, and be secured to a length of the rod 46, and the second or lower portion 62 is adapted to engage and be secured to, the associated symphysis blade post 24. More specifically, the first or upper portion 60 comprises a hollow tube defining an aperture 64 (FIG. 2) configured and dimensioned to receive within and be slidable along a length of the free end of the rod 46. The aperture 64 is preferably circular and of constant diameter, its inside diameter snugly fitting the outside diameter of the free end of the rod 46. Preferably the first or upper portion 60 contains a plurality of outwardly projecting retention knobs 66 on the exposed outer surface thereof, the retention knobs 66 facilitating locking of the first or upper portion 60 of the intermediate member 16 to the rod 46 of the ramus blade 14 with a dental cement (not shown) such as acrylic cement.

The second or lower portion 62 of the intermediate member 16 comprises a socket or aperture 70 (FIG. 2) configured and dimensioned to receive an associated symphysis blade post 24. The interior of socket 70 may be circular, rectangular, or of any other configuration adapted to fit, preferably snugly, over the post 24; however, preferably both the interior of socket 70 and the exterior of post 24 are of circular cross-section so that the intermediate member 16 is rotatable laterally about the axis of the post 24. The peripheral or external configuration of the socket 70 may be rectangular (as shown) or of any other configuration.

Intermediate member 16 may be formed by prefabricating a hollow tube in hard wax or acrylic, securing it to a socket molded to seat on the available post 24, and forming a casting therefrom.

It will be noted that the ramus blade rod 46 comprises a first telescoping part and the upper portion 60 of the intermediate member 16 comprises a second telescoping part. Thus, the embodiment is characterized by one or more of the following two features: the first telescoping part (defined by the male or second ramus blade portion 44) telescopes into the second telescoping part (aperture 64 defined by the intermediate member upper portion 60), and the point of telescopic engagement between the first and second telescoping parts 46, 60 is substantially vertically aligned with, but spaced from, the symphysis blade post 24.

Prior to final connection of an intermediate member 16 to its associated blade members 12, 14, adhesive means (not shown) such as conventional dental cement may be applied both in the aperture 70 of the intermediate member lower portion 62, and in the aperture 64 and about the outer surface and knobs 66 of the intermediate member upper portion 60 to eventually secure the intermediate member lower portion 62 to its associated symphysis blade post 24 and the intermediate member upper portion 60 to the ramus blade rod 46. For enhanced retention of the intermediate member 16 to the symphysis blade 10, the intermediate member socket 70 may be provided with a tiny aperture 72 extending generally horizontally through the walls of the socket 70 and across the portion of the socket 70 which will eventually be occupied by the post 24. Prior to final seating of the socket 70 on the post 24, the socket 70 is placed over the post 24 and a mark is used to indicate the points of the post surface aligned with the tiny aperture 72. Then the socket 70 is removed from the post 24, and a tiny aperture 74 drilled through the post 24 so as to connect the two markings. Then, after the socket 70 is finally seated on the post 24, a transfixation pin 76 (FIG. 2) is passed through the registering apertures 72, 74 and flattened out on the labial and lingual aspects to be flush with the exposed surface of the socket 70, thus automatically locking the socket 70 to the post 24 and reenforcing the cement seal.

Except for the aluminous porcelain about the blade neck portions 26, 48, the implant 10 is preferably formed of a single metal to avoid intimate contact of dissimilar metals in the oral cavity and a resultant possible electrolytic action detrimental to bone. A variety of conventional dental metals may be used for this purpose, the preferred being a castable cobalt-chromium-molybdenum alloy described in Surgical Implant Material ASTM (American Society for Testing and Materials) F75-67, and available under the trade name VITALLIUM. Such alloys are preferred because they are readily cast. However, other materials approved by ASTM for surgical implants may also be used, such as a titanium-aluminum-vanadium alloy (ASTM F136-70), stainless steel (ASTM F55-71), and titanium (ASTM F67-66). While the latter materials are comparable to the castable cobalt-chromium-molybdenum alloys in both physical and chemical properties, they require machining or stamping, rather than casting, thus increasing the cost of manufacture of the implant.

Assembling of the implant within the patient's mouth is relatively simple due to quality of the bone in the ramus. Beneath the cortical plate of bone in the ramus, the bone is loosely assembled and fairly soft so that, after insertion of the ramus blade through the cortical plate of bone, it is relatively easy to move the ramus blade vertically. Thus, for assembly, the first portion 20 of the single double posted symphysis blade 10 is tapped into a thin groove previously formed in the symphysis bone 22. Then the first portion 40 of the ramus blade 14 is tapped into a thin groove previously formed in the ramus bone 42. The ramus blade 14 is tapped in an oblique fashion on the buccal side of the ramus bone 42 in order to avoid the neurovascular bundle that exists on the lingual side. The ramus blade 14 is inserted at an angle approximately 15° higher than ultimately desired. After an initial try-on, the ramus blade 14 is removed and the rod 46 is trimmed as necessary to an appropriate length so that the intermediate member 16 may finally be positioned vertically above the post 24 without the rod 46 extending therebeyond. Then the ramus blade first portion 40 is reinserted as described before. Dental cement is next applied to the interior of the intermediate member socket 70 and to the interior and exterior of the intermediate member upper portion 60 (including retention knobs 66). The upper portion 60 is then slipped over the free end of the rod 46 and slid along the length thereof until it is vertically aligned with post 24. The intermediate member upper portion 60 is then lightly tapped into place, causing the ramus blade first portion 40 to reposition itself below the ramus bone groove as well as connecting and locking the whole implant 10 together. As earlier indicated, a transfixation pin 76 may then be inserted through the aligned tiny apertures 72, 74 of the intermediate member socket 70 and the symphysis blade post 24 to strengthen the cement seal therebetween. After the cement dries, a final prosthesis or bridge may be secured to the implant using conventional techniques, the final prosthesis or bridge being either fixed or removable as preferred.

It will be noted that the final assembly of the implant 10 in the patient's mouth is rendered simple by the combination of the inherent property of the ramus bone (which enables vertical movement of the ramus blade) and the rotatable nature of the engagement between the intermediate member and the symphysis blade (which enables lateral movement of the intermediate member). The combination enables the endosteal portions thereof to be placed in position and connected in a totally passive fashion (i.e., without the creation of lateral torque) and without any bending of the intermediate member.

Insertion and assembly of the implant in the patient's mouth is executed more easily and more rapidly than with conventional implants, with far less trauma to the ramus and symphysis bones. The telescopic nature of the connections between the intermediate member and its associate blades provides a structural strength capable of withstanding the forces generated during mastication. Furthermore, each side of the full implant is totally independent of the other so that if the ramus bone on one side of the mouth should fail, the ramus blade and intermediate member on that side may be removed without disturbing either the symphysis blade or the ramus blade and intermediate member on the other side of the mouth. In three months, after the failed ramus bone is regenerated, a ramus blade may be reinserted in the regenerated ramus bone and connected to the symphysis blade by means of the intermediate member.

The embodiments of the present invention described above are particularly useful where there is no pre-existing mandibular anterior abutment for the implant. Described below are embodiments of the present invention adapted for use with a pre-existing mandibular anterior abutment, i.e., a projecting natural or artificial symphysis bone extension. Exemplary of the situations in which these embodiments of the implant may be used advantageously is the case where a sub-periosteal implant has failed, thus necessitating removal of the posterior posts and struts while leaving the anterior or symphysis bone post in function. Another case involves the mouth where strong anterior teeth remain, but posterior teeth are missing or where there are exposed nerves in the posterior region and the symphyseal-rami endosteal implant must be used to space a prosthesis above the exposed nerves. In the former case, the pre-existing anterior implant serves as the anterior abutment, and in the latter case an existing tooth can be utilized as the anterior abutment. And, of course, even where there is no pre-existing projecting natural or artificial symphysis bone extension to serve as the anterior abutment for the symphyseal-rami endosteal implant of this embodiment, a symphysis blade similar to symphysis blade 12 of the first embodiment may be first implanted to serve as the anterior abutment.

In the embodiment adapted for use with at least one anterior abutment, the implant comprises at least one ramus blade and at least one connecting means adapted to connect the ramus blade to an associated anterior abutment. In the fully assembled implant the connecting means is in effect an intermediate member (identical to intermediate member 16) connecting the ramus blade (identical to ramus blade 14) with an anterior abutment (which may be a symphysis blade like symphysis blade 12, and, more particularly, a post 24 thereof). Preferably both the interior of the socket portion of the connecting means and the exterior of the anterior abutment are of circular cross-section so that the connecting means is rotatable laterally about the axis of the anterior abutment.

As previously indicated, the anterior abutment may be either the upwardly projecting post of a preexisting symphysis blade or an upwardly projecting part of a natural tooth. (It will be noted that the symphysis blade used as an anterior abutment may be merely a portion of a previously existing sub-periosteal implant with lateral portions removed.) The pre-existing anterior abutment, whether natural or artificial, may be ground or otherwise modified to provide a suitable height and a configuration upon which the connecting means is rotatable laterally.

To summarize, the present invention provides an implant which contains endosteal portions which may be easily and rapidly placed into the bone in a totally passive fashion, but which are connected in a manner that provides sufficient strength to withstand the forces generated during mastication.

Now that the preferred embodiments of the present invention have been shown and described in detail, various modifications and improvements thereon will become readily apparent to those skilled in the art. Accordingly, the spirit and scope of the present invention is to be limited only by the appended claims, and not by the foregoing disclosure.

We claim:

1. A symphyseal-rami endosteal implant comprising
   A. a symphysis blade having a first portion adapted to be received in the symphysis bone and a second portion defining at least one projecting post;
   B. a ramus blade having a first portion adapted to be received in a ramus bone and a second portion defining a rod adapted to extend generally parallel to the occlusal plane when said ramus blade first portion is received in the ramus bone; and
   C. an intermediate member for connecting said ramus blade to said symphysis blade and having generally vertically aligned first and second portions, said first portion being adapted to engage, slide longitudinally with respect to, and be secured to a length of said rod and said second portion being adapted to engage and be secured to said associated symphysis blade post.

2. The implant of claim 1 wherein said symphysis blade has a spaced pair of said projecting posts and said implant has a pair of said ramus blades and a pair of said intermediate members, each of said intermediate members being associated with a different one of said ramus blades and a different one of said posts.

3. The implant of claim 1 wherein a portion of said ramus blade intermediate said first and second portions thereof has a tissue-protective outer coating of aluminous porcelain thereon.

4. The implant of claim 1 wherein a portion of said symphysis blade intermediate said first and second portions thereof has a tissue-protective outer coating of aluminous porcelain thereon.

5. The implant of claim 1 additionally including adhesive means securing said intermediate member second portion to its associated symphysis blade post and said intermediate member first portion to its associated rod.

6. The implant of claim 1 wherein said intermediate member second portion and its associated symphysis blade post have registering apertures extending generally horizontally therethrough; and wherein said implant additionally includes at least one transfixation pin passing through said registering apertures to secure said intermediate member to said symphysis blade.

7. The implant of claim 5 wherein said intermediate member second portion and its associated symphysis blade post have registering apertures extending generally horizontally therethrough; and wherein said implant additionally includes at least one transfixation pin passing through said registering apertures to secure said intermediate member to said symphysis blade.

8. The implant of claim 1 wherein said intermediate member is rotatable about the longitudinal axis of its associated symphysis blade post.

9. The implant of claim 6 wherein said intermediate member is rotatable about the longitudinal axis of its associated symphysis blade post.

10. The implant of claim 7 wherein said intermediate member is rotatable about the longitudinal axis of its associated symphysis blade post.

11. The implant of claim 1 wherein said intermediate member first portion and said rod are adapted to engage each other at a point vertically aligned with, but spaced from, said symphysis blade post.

12. The implant of claim 8 wherein said intermediate member first portion and said rod are adapted to engage each other at a point vertically aligned with, but spaced from, said symphysis blade post.

13. The implant of claim 1 wherein said rod telescopes into said intermediate member first portion.

14. The implant of claim 8 wherein said rod telescopes into said intermediate member first portion.

15. The implant of claim 11 wherein said rod telescopes into said intermediate member first portion.

16. The implant of claim 12 wherein said rod telescopes into said intermediate member first portion.

17. A symphyseal-rami endosteal implant adapted for use with at least one anterior abutment comprising
   A. at least one ramus blade having a first portion adapted to be received in a ramus bone and a second portion defining a rod adapted to extend generally parallel to the occlusal plane when said ramus blade first portion is received in the ramus bone; and
   B. at least one means for connecting said ramus blade to an associated anterior abutment, said connecting means having generally vertically aligned first and second portions, said first portion being adapted to engage, slide longitudinally with respect to, and be secured to a length of said rod and said second portion being adapted to engage and be secured to, the associated anterior abutment.

18. The implant of claim 17 wherein said connecting means second portion is adapted to telescopically cooperate with the associated anterior abutment.

19. The implant of claim 17 wherein a portion of said ramus blade intermediate said first and second portions thereof has a tissue-protective outer coating of aluminous porcelain thereon.

20. The implant of claim 17 additionally including adhesive means securing said connecting means second portion to its associated anterior abutment and said connecting means first portion to its associated rod.

21. The implant of claim 17 wherein said connecting means is rotatable about the longitudinal axis of its associated anterior abutment.

22. The implant of claim 18 wherein said connecting means is rotatable about the longitudinal axis of its associated anterior abutment.

23. The implant of claim 17 wherein said rod telescopes into said connecting means first portion.

24. The implant of claim 17 wherein said connecting means first portion and said rod are adapted to engage each other at a point vertically aligned with, but spaced from the associated anterior abutment.

25. The implant of claim 23 wherein said connecting means first portion and said rod are adapted to engage each other at a point vertically aligned with, but spaced from the associated anterior abutment.

26. The implant of claim 17 wherein the anterior abutment comprises the post of a symphysis blade.

27. The implant of claim 17 wherein the anterior abutment comprises a tooth.

28. The implant of claim 17 adapted for use with a spaced pair of anterior abutments, wherein said implant has a pair of said ramus blades and a pair of said connecting means, each of said connecting means being associated with a different one of said ramus blades and a different one of the anterior abutments.

29. The implant of claim 28 wherein the anterior abutments comprise the posts of a symphysis blade.

30. The implant of claim 28 wherein the anterior abutments comprise teeth.

* * * * *